(12) United States Patent
Shilling et al.

(10) Patent No.: US 10,413,734 B2
(45) Date of Patent: Sep. 17, 2019

(54) DYNAMIC CAPTURE MANAGEMENT SAFETY MARGIN

(71) Applicant: Medtronic, Inc., Minneapolis, MN (US)

(72) Inventors: Eric A Shilling, Ham Lake, MN (US); Karen J Kleckner, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 56 days.

(21) Appl. No.: 15/419,212

(22) Filed: Jan. 30, 2017

(65) Prior Publication Data

US 2017/0232262 A1   Aug. 17, 2017

Related U.S. Application Data

(60) Provisional application No. 62/294,219, filed on Feb. 11, 2016.

(51) Int. Cl.
*A61N 1/37* (2006.01)
*A61N 1/368* (2006.01)

(52) U.S. Cl.
CPC ......... *A61N 1/3712* (2013.01); *A61N 1/3684* (2013.01)

(58) Field of Classification Search
CPC .................................................. A61N 1/3712
See application file for complete search history.

(56) References Cited

U.S. PATENT DOCUMENTS

| | | |
|---|---|---|
| 4,428,378 A | 1/1984 | Anderson et al. |
| 4,932,406 A | 6/1990 | Berkovits |
| 4,944,298 A | 7/1990 | Sholder |
| 5,052,388 A | 10/1991 | Sivula et al. |
| 5,144,949 A | 9/1992 | Olson |
| 5,201,865 A | 4/1993 | Kuehn |
| 5,318,594 A | 6/1994 | Limousin et al. |
| 5,507,782 A | 4/1996 | Kieval et al. |
| 5,601,615 A | 2/1997 | Markowitz et al. |
| 5,713,933 A | 2/1998 | Condie et al. |
| 5,741,311 A | 4/1998 | McVenes et al. |

(Continued)

FOREIGN PATENT DOCUMENTS

| | | |
|---|---|---|
| EP | 0990451 A2 | 5/2000 |
| EP | 1 136 098 A2 | 9/2001 |
| WO | 2006/069032 A1 | 6/2006 |

OTHER PUBLICATIONS

(PCT/US2017/016467) PCT Notification of Transmittal of the International Search Report and the Written Opinion of the International Searching Authority, dated Apr. 23, 2017, 13 pages.

*Primary Examiner* — Tammie K Marlen (57) ABSTRACT

A cardiac stimulation system and associated capture management method are provided in which capture and device longevity are improved. The device determines a series of capture thresholds. Capture threshold is the minimum pulse level (pulse energy or pulse amplitude or pulse width) that captures the heart. Each determination requires delivery of pacing pulses at several (at least two) known levels (pulse energy, pulse amplitude and/or pulse width) over time. The individual determined capture thresholds are combined into a set and the variability of the set is used to set the safety margin. The greater the variability in the capture thresholds, the bigger the safety margin.

10 Claims, 3 Drawing Sheets

(56) References Cited

U.S. PATENT DOCUMENTS

| | | |
|---|---|---|
| 5,766,229 A | 6/1998 | Bornzin |
| 5,843,137 A | 12/1998 | Condie et al. |
| 5,861,013 A | 1/1999 | Peck et al. |
| 5,871,512 A | 2/1999 | Hemming et al. |
| 5,873,898 A | 2/1999 | Hemming et al. |
| 5,902,325 A | 5/1999 | Condie et al. |
| 6,067,472 A | 5/2000 | Vonk et al. |
| 6,134,473 A | 10/2000 | Hemming et al. |
| 6,144,881 A | 11/2000 | Hemming et al. |
| 6,163,724 A | 12/2000 | Hemming et al. |
| 6,317,633 B1 | 11/2001 | Jorgenson et al. |
| 6,430,441 B1 | 8/2002 | Levine |
| 6,456,878 B1 | 9/2002 | Yerich et al. |
| 6,456,879 B1 | 9/2002 | Weinberg |
| 6,456,882 B1 | 9/2002 | Schloss |
| 6,587,723 B1 | 7/2003 | Sloman et al. |
| 6,643,549 B1 | 11/2003 | Bradley et al. |
| 6,697,673 B1 | 2/2004 | Lu |
| 6,714,819 B1 | 3/2004 | Sloman |
| 6,772,005 B2 | 8/2004 | Casavant et al. |
| 6,865,422 B1 | 3/2005 | Sloman et al. |
| 6,915,164 B2 | 7/2005 | Bradley et al. |
| 6,975,904 B1 | 12/2005 | Sloman |
| 7,035,687 B1 | 4/2006 | Levine et al. |
| 7,181,280 B1 | 2/2007 | Sloman |
| 7,555,336 B2 | 6/2009 | Sheth et al. |
| 7,684,863 B2 | 3/2010 | Parikh et al. |
| 7,783,355 B2 | 8/2010 | Rueter |
| 7,831,303 B2 | 11/2010 | Rueter et al. |
| 8,565,879 B2 | 10/2013 | Brisben et al. |
| 8,744,579 B2 | 6/2014 | Parikh et al. |
| 8,750,998 B1 | 6/2014 | Ghosh et al. |
| 8,781,584 B2 | 7/2014 | Demmer et al. |
| 8,923,966 B2 | 12/2014 | Brisben et al. |
| 2003/0014084 A1 | 1/2003 | Van Hout |
| 2003/0083700 A1 | 5/2003 | Hill |
| 2003/0083710 A1 | 5/2003 | Ternes et al. |
| 2003/0195579 A1 | 10/2003 | Bradley et al. |
| 2004/0054382 A1 | 3/2004 | Zhu |
| 2005/0137632 A1 | 6/2005 | Ding et al. |
| 2005/0209649 A1 | 9/2005 | Ferek-Petric |
| 2010/0198295 A1* | 8/2010 | Sheldon .............. A61N 1/371 607/28 |
| 2011/0245890 A1 | 10/2011 | Brisben et al. |

* cited by examiner

DYNAMIC CAPTURE MANAGEMENT SAFETY MARGIN

CROSS-REFERENCE TO RELATED APPLICATIONS

This application claims the benefit of U.S. Provisional Application Ser. No. 62/294,219 by Schilling et. al, which was filed on Feb. 11, 2016, and is titled "DYNAMIC CAPTURE MANAGEMENT SAFETY MARGIN." U.S. Provisional Application Ser. No. 62/294,219 is incorporated herein by reference in its entirety.

FIELD

The present disclosure relates generally to the field of implantable cardiac stimulation devices, and, more particularly, to a method for improving capture and device longevity by using a safety margin algorithm that sets the safety margin based on the historical variability of a measured threshold.

BACKGROUND

Cardiac stimulation devices deliver appropriately timed electrical stimulation pulses to a patient's heart to maintain a normal heart rhythm or improve synchronization of heart chambers. Patients having bradycardia, abnormalities of the heart's natural conduction system, a propensity for arrhythmias, cardiac-related breathing disorders, hemodynamic insufficiency, or other cardiac-related conditions may benefit from cardiac pacing therapies delivered in one or more heart chambers.

In order to effectively pace the heart, an electrical impulse delivered to the heart must have sufficient energy to depolarize the myocardial cells. Depolarization of the myocardial cells in response to a pacing pulse is often referred to as "capture." The cardiac electrogram signal evidencing capture, which is a P-wave in the atria or an R-wave in the ventricles, is generally referred to as an "evoked response." The lowest pacing pulse energy that captures the heart may be referred to as the "capture threshold". The amplitude and duration of a pacing pulse is preferably set to produce a pacing pulse energy somewhat greater than the capture threshold in order to ensure effective cardiac pacing over time.

In order to prolong the battery life of the implanted cardiac stimulation device, it is desirable to program the pacing pulse energy to be a minimum value that is considered safely above the pacing threshold. Therefore, the pacing pulse amplitude is commonly set equal to the measured pacing threshold along with a safety margin that ensures capture despite small fluctuations that may occur in the pacing threshold.

Pacing threshold can change over time due to tissue encapsulation of the pacing electrodes, lead movement, changes in the patient's clinical condition, changes in medical therapy, or other causes. A rise in pacing threshold can result in loss of capture and ineffective pacing therapy. Modern pacemakers typically include automatic pacing threshold search algorithms that automatically adjust the pacing pulse energy to ensure pacing pulses remain above the pacing threshold, even if it varies over time. A pacing threshold search may deliver pacing pulses starting at an initially high pulse energy that is greater than the pacing threshold and then progressively decrease the pulse energy until capture is lost. The lowest pulse energy at which capture still occurs is determined as the pacing threshold.

Thus, capture management systems typically include monitoring for changes in the pacing threshold and monitoring for evidence of capture during pacing. Capture monitoring may be performed continuously or periodically and typically involves sensing an evoked P-wave or R-wave following pacing pulse delivery. If loss of capture is detected, a pacing threshold search is performed and a new pacing pulse energy is set based on the pacing threshold search result and the programmed safety factor.

The safety margin is typically established using a fixed value that is programmable by the clinician. U.S. Pat. No. 7,783,355, issued to Rueter, uses a safety factor to adjust the pacing pulse. The device monitors for indicators of a likely increase in pacing threshold. Thereafter, a safety factor is increased and then used in setting a pacing pulse output energy if an indicator of increased pacing threshold is detected.

A dynamically variable safety margin is proposed in U.S. Pat. No. 6,456,882, issued to Schloss. An automatic capture/threshold capability is generally disclosed wherein the safety margin is periodically increased or decreased according to the performance of the stimulation device, i.e., based upon the frequency of capture. In U.S. Pat. No. 6,456,879, issued to Weinberg, a method is generally disclosed for altering stimulation energy based on rheobase and/or chronaxie shift of a strength-duration curve. The strength-duration curve may be divided into two regions having differently sized safety margins.

There remains a need to improve capture management and device longevity. It is therefore desirable to develop additional capture algorithms that improve capture management while extending device longevity.

BRIEF SUMMARY

The present disclosure provides a cardiac stimulation system and associated capture management method that includes a safety margin algorithm. One or more embodiments relate to the device determining a series of capture thresholds. Capture threshold means the minimum pulse level (i.e. pulse energy, pulse amplitude, and/or pulse width) that captures the heart. Each determination requires delivery of pacing pulses at several or at least two known levels (pulse energy, pulse amplitude and/or pulse width) over time. The individual determined capture thresholds are combined into a set and the variability of the set is used to set the safety margin. The greater the variability in the capture thresholds, the bigger the safety margin.

One or more embodiments relate to providing capture management in an implantable medical device. A cardiac pacemaker is employed to repeatedly determine capture thresholds of a chamber of a patient's heart. Stored in memory are the determined capture thresholds to produce a set of determined capture thresholds. A determination is made as to the historical variability of the set of determined capture thresholds. A safety margin is set using the historical variability of the determined capture thresholds. The set safety margin is used to determine a pacing pulse level and subsequently pacing the chamber of the patient's heart at the pulse level.

One or more embodiments relate to a safety margin algorithm configured to set a safety margin based on historical variability of a measured threshold. The historical variability of the measured threshold is assessed based on a rolling window (e.g. 14-day maximum (max) and 14-day minimum (min)) of the measured capture threshold. A rolling window is a function that focuses on a set of data such that new data continues to be added to the window while the oldest data can be removed.

In one or more embodiments, the safety margin is set to 0.5V above the last measured threshold if the difference between the 14 day max and the 14 day min was less than 0.5V. One or more other embodiments relate to a condition in which the difference between the 14 day max and min was ≥0.5V but less than 1.0V, thereby establishing the safety margin to be set to about 1.0V above the last measured threshold. One or more other embodiments relate to a condition that if the difference between the 14 day max and min was ≥1.0V, the safety margin is set to be about 1.5V above the last measured threshold. If there are fewer than 5 valid threshold measurements, indicating a scarcity of data on which to base a variability calculation, the adaptive amplitude can be set conservatively to be about 1.5V above the last measured threshold. Alternate approaches for calculating the historical variability could include different windowing schemes (e.g. 7-day max/min rolling window instead of a 14-day max/min rolling window), use of averages and standard deviations, or other statistical measures of variability.

DETAILED DESCRIPTION OF THE PREFERRED EMBODIMENTS

The present disclosure is directed to capture management for the left ventricle, right ventricle or the atrium. The safety margin used in setting the output pulse energy is automatically adjusted in response to detecting pre-specified conditions.

The present disclosure is useful in both atrial and/or ventricular stimulation applications. Thus, the present disclosure may be realized in single, dual, or multichamber cardiac stimulation devices, capable of delivering a cardiac pacing therapy. The term "cardiac pacing therapy" is used herein to refer to any cardiac stimulation therapy that employs relatively low-energy stimulation pulses to depolarize the myocardial tissue to achieve a therapeutic effect. Cardiac pacing therapies may include but are not limited to, bradycardia pacing, cardiac resynchronization therapy, extra systolic stimulation therapies, overdrive pacing for treating or preventing arrhythmias or cardiac-related disordered breathing, and anti-tachycardia pacing therapies.

Figure 1:
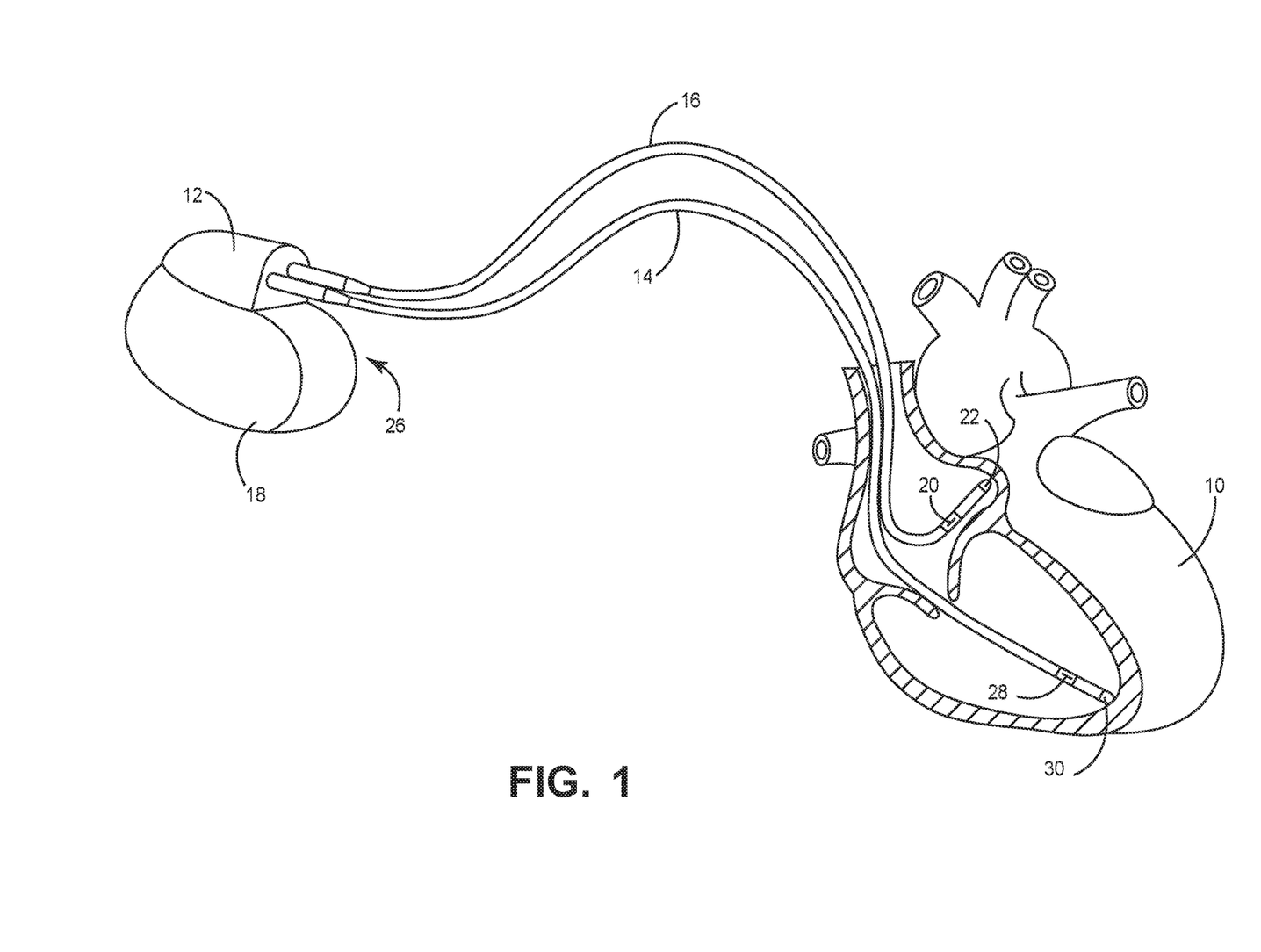
FIG. 1 is an illustration of an exemplary cardiac stimulation device in which the present disclosure may be usefully practiced.

FIG. 1 is an illustration of an exemplary cardiac stimulation device in which the present invention may be usefully practiced. Many other device configurations can also implement the present disclosure such as the cardiac devices described in U.S. Pat. No. 8,750,998, incorporated herein by reference in its entirety. The external configuration of a dual chamber cardiac stimulation device 26 (or implantable medical device (IMD), which is provided with a hermetically sealed enclosure 18, typically fabricated of biocompatible metal such as titanium. Mounted to the top of the enclosure 18 is a connector block assembly 12, which receives electrical connectors located on the proximal ends of leads 14 and 16. The combination of the leads 14 and 16 and the device 26 constitute an implantable cardiac stimulation system. A dual chamber cardiac stimulation device in which the present invention may be implemented is generally described in U.S. Pat. No. 5,507,782, issued to Kieval et al., which is hereby incorporated herein by reference.

Lead 16 is an atrial bipolar cardiac stimulation and sensing lead, carrying two electrodes 20 and 22. Electrodes 20 and 22 are used both to sense atrial depolarizations (P-waves) and to deliver atrial stimulation pulses. Atrial stimulation pulses may be delivered between electrodes 20 and 22 in a bipolar mode or between electrode 22 and the housing 18 of device 26 in a unipolar mode. Sensing of P-waves may occur between electrode 20 and electrode 22 in a bipolar sensing mode or between either of electrode 20 and 22 and the housing 18 of device 26 in a unipolar sensing mode.

Similarly, lead 14 represents a ventricular bipolar cardiac stimulation and sensing lead, carrying two electrodes 28 and 30. Electrodes 28 and 30 are used to sense and stimulate the ventricle. Sensing of ventricular depolarizations (R-waves) may be accomplished between electrodes 30 and 28 in a bipolar sensing mode or between either of electrodes 30 and 28 and the housing 18 of device 26 in a unipolar sensing mode. Bipolar ventricular stimulation may be accomplished between electrodes 30 and 28 or unipolar ventricular stimulation may be accomplished between electrode 30 and the conductive housing 18 of device 26.

Figure 2:
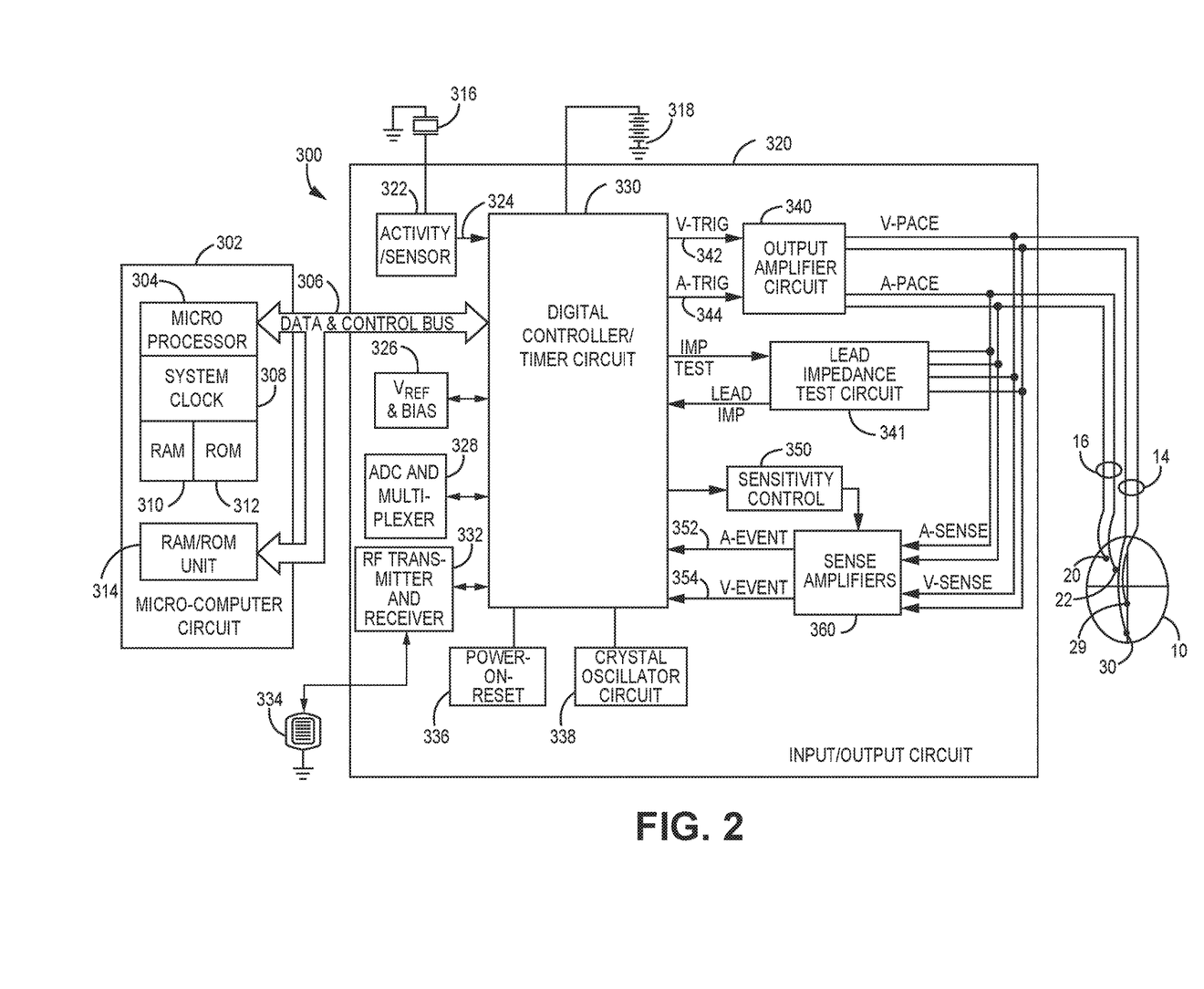
FIG. 2 is a more detailed functional block diagram of the cardiac stimulation device illustrated in FIG. 1.

FIG. 2 is a more detailed functional block diagram of the cardiac stimulation device illustrated in FIG. 1. The device circuit 300 is located within housing 18 of device 26 as illustrated in FIG. 1. The bipolar leads 14 and 16 are illustrated schematically as coupled directly to the input/output circuit 320. However, in the actual implantable device they would, of course, be coupled by means of removable electrical connectors inserted in the connector block 12 illustrated in FIG. 1.

Circuit 300 is divided generally into a microcomputer circuit 302 and an input/output circuit 320. An output amplifier circuit 340 includes a ventricular pulse generator circuit coupled to the ventricle of the heart 10 by means of electrodes 28 and 30 on lead 16 as well as an atrial pulse generator circuit coupled to the atrium of heart 10 by means of atrial electrodes 20 and 22, located on lead 14. Similarly, sense amplifier circuit 360 includes atrial and ventricular sense amplifiers coupled to the atrium and ventricle, respectively, by means of leads 14 and 16. The output circuit 340 and sense amplifier circuit 360 may contain pulse generators and sense amplifiers, respectively, corresponding to any of those presently employed in commercially available cardiac pacemakers.

Sensed atrial depolarizations (or P-waves) that are detected by the atrial sense amplifier, in response to an atrial signal received from atrial lead 14 exceeding an atrial P-wave sensing threshold, are communicated to the digital controller/timer circuit 330 on A-event line 352. Similarly, ventricular depolarizations (or R-waves) that are detected by the ventricular sense amplifier, in response to a ventricular signal received from ventricular lead 16 exceeding a ventricular R-wave sensing threshold, are communicated to the digital controller/timer circuit 330 on V-event line 354. In devices configured for the detection of arrhythmias, consecutively sensed R-waves and P-waves may be used for measuring various intervals, such as R-R intervals, P-P intervals, R-P intervals and P-R intervals, for use in detecting arrhythmias as will be described in greater detail below.

In the absence of a sensed event prior to the expiration of a related escape interval, a pacing pulse will be generated by input/output circuit 320. In order to trigger generation of a ventricular pacing pulse, digital controller/timer circuit 330 generates a trigger signal on V-trig line 342. Similarly, in order to trigger an atrial pacing pulse, digital controller/timer circuit 330 generates a trigger pulse on A-trig line 344.

Control of timing and other functions within the input/output circuit 320 is provided by digital controller/timer circuit 330, which includes a set of timers and associated logic. Digital controller/timer circuit 330 defines the basic pacing or escape intervals controlling the timing of atrial and ventricular pacing pulse delivery. An A-A escape interval is initiated on atrial sense (A-event) or atrial pace (A-pace) events. An atrial pacing pulse (A-pace) is triggered at the expiration of the A-A escape interval. A V-V escape interval is initiated on ventricular sense (V-event) or pace (V-pace) events, and a ventricular pulse pacing (V-pace) is triggered upon the expiration thereof. Digital controller/timer circuit 330 also defines A-V intervals that commence following a sensed A-event or a delivered A-pace, and upon the expiration thereof a ventricular pacing pulse is triggered during atrial synchronized pacing modes. The specific values of the escape intervals defined by timer circuit 330 are controlled by the microcomputer circuit 302 by means of data and control bus 306 according to programmed parameter values and operating modes.

A variety of mode switching features have been disclosed or implemented in commercially available devices which respond to an excessively rapid atrial rhythm by causing the pacing system to switch from an atrial synchronized pacing mode, such as DDD/DDDR, to a non-synchronized mode such as VVI/VVIR or DDI/DDIR. Such mode switching features are disclosed in U.S. Pat. No. 5,144,949, by Olson, U.S. Pat. No. 5,318,594, by Limousin et al., U.S. Pat. No. 4,944,298, by Sholder, and U.S. Pat. No. 4,932,406 by Berkovits, all incorporated herein by reference in their entireties. In such pacing systems, the primary purpose of the mode switch is to prevent the pacing system from tracking a non-physiologic atrial rate.

Digital controller/timer circuit 330 also controls sensitivity settings of the sense amplifiers 360 by means of sensitivity control 350 and defines time intervals for controlling operation of the atrial and ventricular sense amplifiers in sense amplifier circuit 360. A number of blanking and refractory intervals are typically defined, as is well known in the art, for controlling the sensing functions of sense amplifiers 360 and for controlling how digital timer/controller circuit 330 responds to sensed events.

For example, an atrial refractory sensed event occurring during a post ventricular atrial refractory period (PVARP) may trigger a non-competitive atrial pacing (NCAP) period during which no atrial pacing pulse may occur. The non-competitive atrial pacing period is intended to prevent triggering of atrial tachycardia by an atrial pacing pulse delivered during the relative refractory period.

In the embodiment illustrated in FIG. 2, device 26 is provided with a sensor 316, which may be a piezoelectric sensor intended to monitor patient activity, in order to allow provision of rate responsive pacing, such that the defined pacing rate (A-A escape interval or V-V escape interval) increases with increased levels of sensed activity. Sensor 316 generates electrical signals in response to sensed physical activity which are processed by activity/sensor circuit 322 and provided to digital controller/timer circuit 330. The present disclosure may also be practiced in non-rate responsive pacemakers.

In alternative embodiments, a physiological sensor 316 and corresponding activity/sensor circuit 322 may alternatively be used for monitoring cardiac hemodynamic performance, myocardial contractile performance, a metabolic state or other physiological condition. Physiological sensors known for use in conjunction with implanted devices may include blood pressure sensors, oxygen saturation sensors, pH sensors, temperature sensors, blood flow sensors, acoustical sensors, accelerometers, impedance sensors and so forth. Signals from such sensors may be processed for determining a need for therapy delivery or therapy adjustment as a physiological condition or metabolic need changes.

Data transmission to and from an external device, commonly known in the art as a "programmer," is accomplished by means of telemetry antenna 334 and an associated RF transmitter and receiver 332, which serves both to demodulate received downlink telemetry and to transmit uplink telemetry. For the purposes of the present disclosure, telemetry circuitry for communicating with an external device may correspond to any telemetry system known for use with implantable medical devices.

Threshold data from threshold searches may be stored in the RAM 310 or the RAM/ROM unit 314 of microcomputer 302 for later telemetry out on command of an external programmer. This data may be encoded in digital form and transmitted via RF transmitter 332 and antenna 334 to an external programmer for display and/or analysis in the form of atrial and ventricular strength-duration curves as described in U.S. Pat. No. 5,601,615, issued to Markowitz et al., hereby incorporated herein by reference in its entirety. Data pertaining to detected capture threshold and historical variability of measured thresholds, which may trigger safety margin adjustments, in accordance with the present invention, may also be stored in RAM 310 for later telemetry out for diagnostic and therapy management purposes.

Crystal oscillator circuit 338 provides the basic timing clock for the input/output circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the input/output circuit 320, while analog to digital converter (ADC) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in currently available implantable cardiac stimulation devices.

Microcomputer 302 controls the operational functions of digital controller/timer 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, A-event and V-event signals.

Microprocessor 304 controls the scheduling of pacing threshold searches, either on a periodic or triggered basis, which are then executed by input/output circuit 320. For example, a pacing threshold search may be executed upon detection of loss of capture. For the purposes of the present disclosure, prior art circuitry and methods for performing pacing threshold searches and capture detection may be implemented in conjunction with the present invention. Examples of appropriate pacing threshold searching methods are generally disclosed in the previously incorporated U.S. Pat. No. 5,601,615 to Markowitz, in U.S. Pat. No. 6,067,472 issued to Vonk et al., in U.S. Pat. No. 5,713,933 issued to Condie et al., or U.S. Pat. No. 6,430,441 issued to Levine et al., all of which patents are incorporated herein by reference in their entirety.

In accordance with the present disclosure, microprocessor 304 executes code stored in associated memory 310 and 312 for detecting indicators of increased pacing threshold and for automatically increasing the safety margin in response to an increased pacing threshold indicator detection. A newly adjusted safety margin is then used by digital timer and controller 330 to cause output circuit 340 to deliver pacing pulses at an output energy set according to the most recent pacing threshold search result and the newly adjusted safety margin.

Device 26 may further include lead impedance measuring circuitry 341 coupled to leads 14 and 16 for monitoring changes in lead impedance. Implantable medical devices capable of measuring and monitoring changes in lead impedance are generally disclosed in U.S. Pat. No. 5,201,865 issued to Kuehn, U.S. Pat. No. 5,741,311 issued to McVenes et al., and U.S. Pat. No. 6,317,633 issued to Jorgenson et al., all of which are incorporated herein by reference in their entirety. A change in lead impedance may occur as the result of shifting or dislodgement of a lead. Such a change may result in a change in pacing threshold and/or may alter sensing characteristics making pacing threshold searches and capture detection algorithms unreliable.

The illustrated device block diagram of FIG. 2 is merely exemplary, and corresponds to the general functional organization of a typical multi-programmable microprocessor controlled DDD(R) cardiac pacemaker. It is believed that the present invention is readily practiced in the context of such a device, and that the present disclosure can therefore readily be practiced using the basic hardware of existing microprocessor controlled dual chamber pacemakers, as presently available, with the disclosure implemented primarily by means of modifications to the software stored in the ROM 312 of the microcomputer circuit 302. However, the present disclosure may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present disclosure should not be understood to be limited to a cardiac stimulation device having an architecture as illustrated in FIG. 2, and a circuit architecture as illustrated in FIG. 2 is not believed to be a prerequisite to enjoying the benefits of the present disclosure.

Furthermore, while a particular dual-chamber implantable cardiac stimulation device and lead system is shown in FIGS. 1 and 2, the present disclosure may be usefully practiced in other types of cardiac stimulation devices such as any single, dual or multi-chamber cardiac stimulation device capable of providing cardiac pacing therapies and may further include higher-voltage stimulation therapies for cardioversion and defibrillation. As such, other types of lead systems may be substituted for the particular lead system shown in FIG. 1 according to the type of cardiac stimulation device implanted. Unipolar, bipolar, and/or multipolar leads provided with tip, ring, and/or coil electrodes may be used. A lead system may be used to position electrodes within the heart or external to the heart such as epicardial or subcutaneous placements.

In some embodiments of the present disclosure, an indicator of increased pacing threshold may be related to the occurrence of an arrhythmia. For example, the atrial substrate is believed to be more difficult to capture after an episode of atrial fibrillation or atrial flutter. The time that the increased pacing threshold is expected to remain higher is thought to be related to the duration of the atrial arrhythmia episode. As such, device 26 may include arrhythmia detection capabilities.

Figure 3:
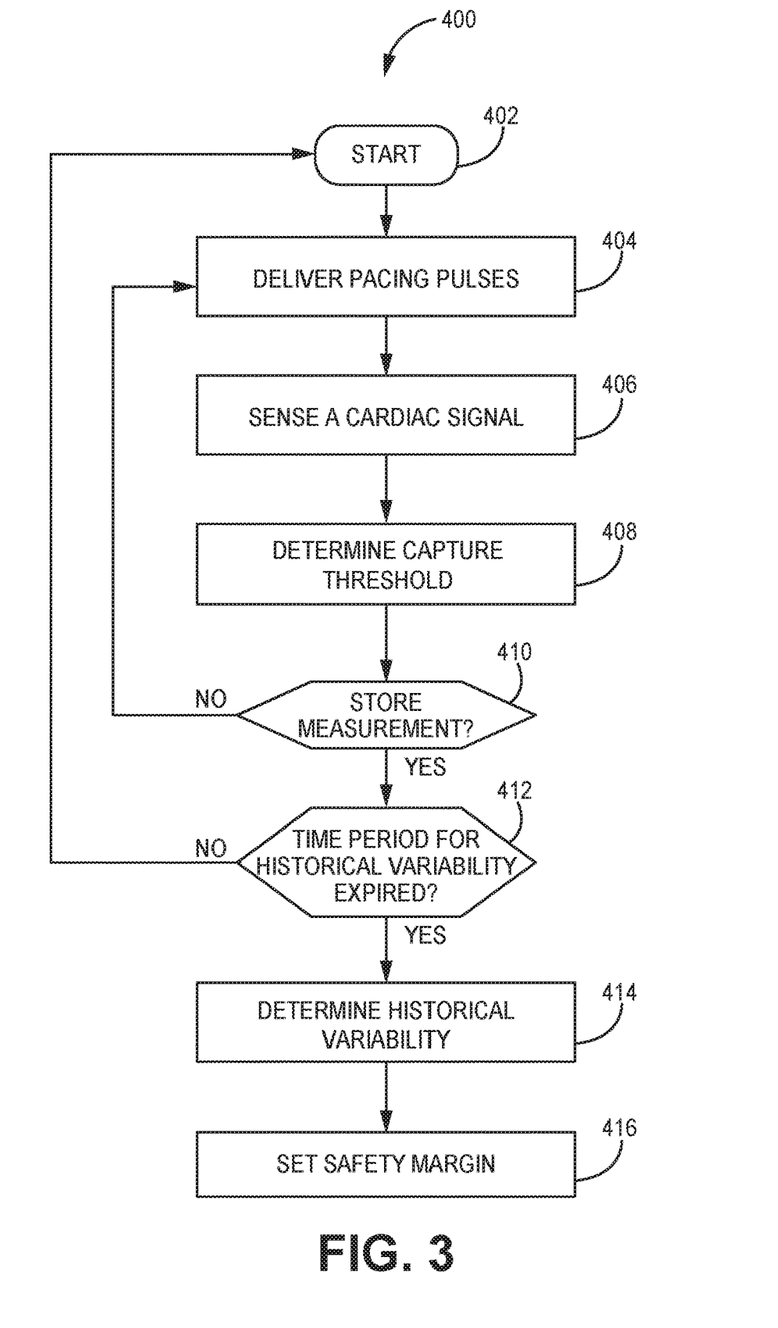
FIG. 3 is a flow diagram providing an overview of a method for improving capture using a safety margin algorithm that sets the safety margin based on the historical variability of a measured threshold in accordance with the present disclosure.

FIG. 3 is a flow diagram providing an overview of a method 400 for automatically adjusting the safety margin in response to detecting one or more conditions. Method 400 may be enabled by a clinician to operate continuously such that the safety margin is adjusted when one of a set of conditions are detected for adapting the pacing amplitude is detected. Method 400 may be operating even when a pacing therapy is not being delivered such that if a pacing therapy becomes necessary the pacing pulse energy delivered will be adequate to capture the heart tissue from the onset of pacing.

At block 402, the process begins for acquiring capture thresholds. At block 404, pacing pulses are delivered to cardiac tissue using a pacing threshold that was previously determined to be effective for that patient. At block 406, a cardiac signal is sensed from an implanted electrode in response to the delivered pacing pulses.

At block 408, the sensed cardiac signal is used to determine whether the delivered pacing pulses captured the heart and the results of the determinations are used to determine a capture threshold.

At block 410, the microprocessor stores the pacing threshold associated with the current measurement. Storing the pacing threshold can be performed automatically or after a certain condition has been met. The condition can be a pre-specified amount of time, a number of pacing thresholds acquired, and/or each pacing threshold can be automatically stored. At block 410, the microprocessor can be configured to determine whether a time period for collecting and storing into the memory an adequate number of captured thresholds to calculate historical variability has expired. The time period can be set to any particular time. In one example, the time is set to a 14 day time period, described in greater detail below. The NO path from block 410 returns to block 402 to deliver another series of pacing pulses. Each time a series of pacing pulses is delivered, any resulting measured or determined capture threshold is stored into memory. After some time, a set of determined capture thresholds will have been stored into memory. For example, a determine capture threshold can be made each day for 14 days. Once the time period has expired for collecting determined capture thresholds, the YES path from block 410 continues to block 412.

At block 412, the microprocessor determines a historical variability of the set of determined capture thresholds. The historical variability of the set of determined capture thresholds comprises a rolling maximum and rolling minimum of the determined threshold over the time period. Rolling maximum involves periodically evaluating a set of numbers and determining the maximum number of that set. The maximum number is periodically re-evaluated as numbers are added or subtracted from the set. In particular, rolling maximum involves comparing the current value to a set of previous values and if larger replaces the maximum with that value. If the set is empty (i.e. no numbers) then the first value is the maximum. Rolling minimum involves periodically evaluating a set of numbers and determining the minimum number of that set. The minimum number is periodically re-evaluated as numbers are added or subtracted from the set. In particular, rolling minimum involves comparing the current value to a set of previous values and if smaller replaces the minimum with that value. If the set is empty (i.e. no numbers) then the first value is the minimum.

At block 414, a safety margin is set using the historical variability of the determined capture thresholds. For setting the safety margin, a difference in pacing capture threshold amplitude between the rolling maximum and the rolling minimum must be determined. In response to determining the difference in amplitude, the predetermined value is selected thereby allowing the safety margin to be determined.

The selected predetermined value depends on a condition of a set of conditions. The set of conditions are listed below. First, the safety margin is set to about 0.5V above a last measured threshold if the difference in amplitude between the rolling maximum and the rolling minimum was less than 0.5. Second, the safety margin is set to about 1.0V when the difference in amplitude between the rolling maximum and the rolling minimum was ≥0.5V but less than 1.0V. Third, the safety margin is set to about 1.5V when a difference between the difference in amplitude between the rolling maximum and the rolling minimum was ≥1.0V. Fourth, if fewer than a pre-specified value of valid threshold measurements are determined to exist, indicating a scarcity of data on which to base a variability calculation, the safety margin is set to a preset value above the last measured threshold. Alternate approaches for calculating the historical variability could include different windowing schemes (ex. 7-day max/min), use of averages and standard deviations, or other statistical measures of variability. Amplitude nominally is set to threshold plus safety margin, or to current amplitude minus a decay constant, whichever is higher. Alternate embodiments could include a different balance between the decay constant and rolling window size. One or more other embodiments involve a second safety margin algorithm. The second safety margin algorithm embodiment involves setting the safety margin in a manner that provides enhanced capture performance compared to the first safety algorithm embodiment that is described relative to FIG. 3. Rather than setting the safety margin to "a value above a last measured threshold," the second embodiment has a safety margin that is configured to be set to "a value above the highest of a set of recently measured thresholds", e.g., the last 14 of recently measured thresholds as exemplarily shown in Table 1. In one or more other embodiments, the cardiac stimulation device 26 could typically operate using the first embodiment safety margin algorithm but then automatically switch to the more conservative method (i.e. adding safety margin to the 14 day maximum) if there are historical indications in the cardiac stimulation device 26 of days in which the less conservative method (i.e. adding the safety margin to the current days measured threshold) is not sufficient. For example, the cardiac stimulation device 26 could track instances in which the current threshold is higher than the current amplitude used for pacing. One switching operation may require a switch from the first to the second embodiment to occur if the current threshold is higher than the current amplitude used for pacing. If that occurs, the cardiac stimulation device 26 could switch to the more conservative method (i.e. adding safety margin to the 14 day max) and use the new pacing threshold. An exemplary threshold history that is tracked by the cardiac stimulation device 26 can comprise a set of thresholds. Each day may have a measured threshold, as shown in Table 1 provided below.

TABLE 1

Exemplary threshold history data

| Time (Day) | Threshold | Maximum |
| --- | --- | --- |
| 1 | Threshold 1 | 1.00 volt (V) |
| 2 | Threshold 2 | 1.50 V |
| 3 | Threshold 3 | 1.25 V |
| 4 | Threshold 4 | 1.50 V |
| 5 | Threshold 5 | 1.00 V |
| 6 | Threshold 6 | 1.00 V |
| 7 | Threshold 7 | 1.00 V |
| 8 | Threshold 8 | 1.00 V |
| 9 | Threshold 9 | 1.00 V |
| 10 | Threshold 10 | 1.00 V |
| 11 | Threshold 11 | 1.25 V |
| 12 | Threshold 12 | 1.25 V |
| 13 | Threshold 13 | 1.00 V |
| 14 | Threshold 14 | 1.50 V |
| Maximum Threshold of the 14 day period | | 1.50 V |

By comparing each threshold in Table 1, it is clear that the maximum threshold is 1.50 V. The pacing threshold is calculated based upon the maximum threshold plus an offset that is determined by a variability level. The level of variability—low, medium or high—is based upon the difference in amplitude between the rolling maximum and the rolling minimum of a certain number of thresholds. For example, low variability is a difference of less than 0.5V in amplitude between a rolling maximum and the rolling minimum. Medium variability is a difference of ≥0.5V but less than 1.0V in amplitude between the rolling maximum and the rolling minimum. High variability is a difference that is ≥1.0V in amplitude between the rolling maximum and the rolling minimum.

If low variability exists between the rolling maximum and the rolling minimum, 0.5V is the offset that is added to the maximum threshold value of 1.50V. Therefore, the pacing amplitude is 1.50V+0.50V which provides a new pacing threshold of 2.0V. If medium variability exists between the rolling maximum and the rolling minimum, then the pacing threshold is increased by 1.0V instead of 0.5V to the maximum threshold over the 14 day time period. If high variability exists between the rolling maximum and the rolling minimum, then 1.50V is added to the maximum threshold over the 14 day time period.

The method and system have been presented for improving capture and device longevity by using a safety margin algorithm. In one or more embodiments, the safety margin algorithm can be less conservative such that is safety margin is applied to the current pacing threshold. In one or more other embodiments, a more conservative approach has a safety margin that is applied to the rolling maximum threshold. In still yet other embodiments, the cardiac stimulation device 26 can automatically switch between the less conservative to the more conservative approaches depending upon certain conditions. For example, switching to the more conservative method (i.e. adding safety margin to the 14 day maximum) can be performed if there are historical indications in the cardiac stimulation device 26 of days in which the less conservative method (i.e. adding the safety margin to the current days measured threshold) is not sufficient.

By using a safety margin algorithm that sets the safety margin based on the historical variability of a measured threshold. The capture performance of the new algorithm is significantly better than current programming observed in the field and comparable to the very conservative method of always using a 1.5V safety margin. The average pacing amplitude that results from the new algorithm can also be significantly lower than both conventional programming observed in the field and nominal programming. A safety margin that is programmed to a static value at a single point in time may not adequately ensure that the safety margin is able to cover periods of extreme variability in pacing capture threshold. Also, a safety margin that is programmed to a static value at a single point in time may result in a pacing amplitude that is significantly higher than is actually needed when pacing thresholds are very stable. By employing a safety margin that substantially captures cardiac tissue but avoids delivering pacing pulses that waste energy, battery life is preserved thereby extending the life of the device.

The following paragraphs enumerated consecutively from 1 through 38 provide for various aspects of the present invention. In one embodiment, in a first paragraph (1), the present invention provides:

Embodiment 1 is a method of providing capture management in an implantable medical device, the method comprising:
 (a) employing a cardiac pacemaker to repeatedly determine capture thresholds of a chamber of a patient's heart;
 (b) storing into memory the determined capture thresholds to produce a set of determined capture thresholds;
 (c) determining a historical variability of the set of determined capture thresholds;
 (d) setting a safety margin using the historical variability of the determined capture thresholds; and
 (e) using the set safety margin to determine a pacing pulse level and subsequently pacing the chamber of the patient's heart at the pulse level.

Embodiment 2 is a method of embodiment 1 wherein the safety margin comprises a last determined capture threshold plus a predetermined value, the last determined capture threshold is latest in time capture threshold stored into memory.

Embodiment 3 is a method according to any of embodiments 1-2 wherein the last determined capture threshold can be a set of capture thresholds measured over a pre-specified time period.

Embodiment 4 is a method according to any of embodiments 1-3 wherein the pre-specified time period is 14 or less consecutive days.

Embodiment 5 is a method according to any of embodiments 1-4 wherein the safety margin comprises a last determined capture threshold multiplied by a factor, the last determined capture threshold is a latest in time capture threshold stored into memory.

Embodiment 6 is a method according to any of embodiments 1-5 wherein the historical variability of the set of determined capture thresholds comprises a rolling maximum and rolling minimum of the measured threshold over the time period.

Embodiment 7 is a method according to any of embodiments 1-2 further comprising:
 determining a difference in amplitude between the rolling maximum and the rolling minimum; and
 selecting the predetermined value in response to the difference in amplitude.

Embodiment 8 is a method according to any of embodiments 1-7 wherein the selected predetermined value depends on a condition of a set of conditions.

Embodiment 9 is a method according to any of embodiments 1-8 wherein the safety margin is set to about 0.5V above a last measured threshold if the difference in amplitude between the rolling maximum and the rolling minimum was less than 0.5V.

Embodiment 10 is a method according to any of embodiments 1-9 wherein the safety margin is set to about 1.0V when the difference in amplitude between the rolling maximum and the rolling minimum is ≥0.5V but less than 1.0V.

Embodiment 11 is a method according to any of embodiments 1-10 wherein the safety margin is set to about 1.5V when a difference between the difference in amplitude between the rolling maximum and the rolling minimum is ≥1.0V.

Embodiment 12 is a method according to any of embodiments 1-11 wherein if fewer than a pre-specified value of valid threshold measurements are determined to exist, the safety margin set to a preset value above the last measured threshold.

Embodiment 13 is a method according to any of embodiments 1-12 wherein the preset value being about 1.5V.

Embodiment 14 is a method of providing capture management in an implantable medical device, the method comprising:
 (a) delivering pacing pulses to cardiac tissue at known pulse levels;
 (b) sensing cardiac signals from an implanted electrode in response to the delivered pacing pulses;
 (c) using the sensed cardiac signal to determine whether the delivered pacing pulses captured the heart and using the results of the determinations to determine a capture threshold;
 (d) repeating steps (a)-(c), over a time period, and storing into memory each determined capture threshold to produce a set of determined capture thresholds;
 (e) determining a historical variability of the set of determined capture thresholds; and
 (f) setting a safety margin using the historical variability of the determined capture thresholds.

Embodiment 15 is an implantable medical device, comprising:
 a pulse generator for delivering pacing pulses;
 at least one implanted electrode in electrical communication with the pulse generator for delivering the pacing pulses to cardiac tissue; and
 a microprocessor for controlling the pulse generator, acquiring sensed data from the at least one implanted electrode, wherein the sensed data includes a determined capture threshold;
 a memory for storing the determined capture thresholds to produce a set of determined capture thresholds, historical variability of a determined capture threshold; and
 a safety margin set based on a historical variability of the determined capture thresholds, the set safety margin to determine a pacing pulse level and subsequently pacing the chamber of the patient's heart at the pulse level.

Embodiment 16 is a device of embodiments 15 wherein the safety margin comprises a last determined capture threshold plus a predetermined value, the last determined capture threshold is a latest in time capture threshold stored into memory.

Embodiment 17 is a device of any of embodiments 15-16 wherein the historical variability of the set of determined capture thresholds comprises a rolling maximum and rolling minimum of the measured threshold over the time period.

Embodiment 18 is a device of any of embodiments 15-17 further comprising:
    determining a difference in amplitude between the rolling maximum and the rolling minimum; and
    selecting the predetermined value in response to the difference in amplitude.

Embodiment 19 is a device of any of embodiments 15-17 wherein the selected predetermined value depends on a condition of a set of conditions.

Embodiment 20 is a method according to any of embodiments 15-18 wherein the safety margin is set to about 0.5V above a last measured threshold if the difference in amplitude between the rolling maximum and the rolling minimum was less than 0.5.

Embodiment 21 is a method according to any of embodiments 15-20 wherein the safety margin is set to about 1.0V when the difference in amplitude between the rolling maximum and the rolling minimum was ≥0.5V but less than 1.0V.

Embodiment 22 is a method according to any of embodiments 15-21 wherein the safety margin is set to about 1.5V when a difference between the difference in amplitude between the rolling maximum and the rolling minimum was ≥1.0V.

Embodiment 23 is a method according to any of embodiments 15-22 wherein if fewer than a pre-specified value of valid threshold measurements are determined to exist, the safety margin set to a preset value above the last measured threshold.

Embodiment 24 is a method according to any of embodiments 15-23 wherein the preset value being about 1.5V.

Embodiment 25 is a device of any of embodiments 15-24 wherein the safety margin comprises a last determined capture threshold multiplied by a factor, the last determined capture threshold is a latest in time capture threshold stored into memory.

Embodiment 26 is a system of providing capture management in an implantable medical device, the system comprising:
    (a) processing means for employing a cardiac pacemaker to repeatedly determine capture thresholds of a chamber of a patient's heart;
    (b) storing means for storing into memory the determined capture thresholds to produce a set of determined capture thresholds;
    (c) processing means for determining a historical variability of the set of determined capture thresholds;
    (d) processing means for setting a safety margin using the historical variability of the determined capture thresholds; and
    (e) processing means for using the set safety margin to determine a pacing pulse level and subsequently pacing the chamber of the patient's heart at the pulse level.

Embodiment 27 is a method comprising:
    with a processor,
    (a) controlling a stimulation generator to deliver electrical stimulation to repeatedly determine capture thresholds of a chamber of a patient's heart;
    (b) storing into memory the determined capture thresholds to produce a set of determined capture thresholds;
    (c) determining a historical variability of the set of determined capture thresholds;
    (d) setting a safety margin using the historical variability of the determined capture thresholds; and
    (e) using the set safety margin to determine a pacing pulse level and subsequently pacing the chamber of the patient's heart at the pulse level.

Embodiment 28 is a computer-readable medium comprising instructions that, when executed by a processor, cause the processor to:
    (a) control a stimulation generator to deliver electrical stimulation to repeatedly determine capture thresholds of a chamber of a patient's heart;
    (b) storing into memory the determined capture thresholds to produce a set of determined capture thresholds;
    (c) determining a historical variability of the set of determined capture thresholds;
    (d) setting a safety margin using the historical variability of the determined capture thresholds; and
    (e) using the set safety margin to determine a pacing pulse level and subsequently pacing the chamber of the patient's heart at the pulse level.

The twenty ninth embodiment relates to a system of providing capture management in an implantable medical device, the system comprising:
    (a) processing means for employing a cardiac pacemaker to repeatedly determine capture thresholds of a chamber of a patient's heart;
    (b) storing means for storing into memory the determined capture thresholds to produce a set of determined capture thresholds;
    (c) processing means for determining a historical variability of the set of determined capture thresholds;
    (d) processing means for setting a safety margin using the historical variability of the determined capture thresholds such that the safety margin is set to a value above a highest of a set of recently measured thresholds; and
    (e) processing means for using the set safety margin to determine a pacing pulse level and subsequently pacing the chamber of the patient's heart at the pulse level.

A thirtieth embodiment relates to an implantable medical device, comprising:
    a pulse generator for delivering pacing pulses;
    at least one implanted electrode in electrical communication with the pulse generator for delivering the pacing pulses to cardiac tissue;
    at least one implanted electrode to sense capture in response to the delivery of the pacing pulses;
    a microprocessor configured to control the pulse generator, acquire sensed data from the at least one implanted electrode(s), wherein the sensed data includes a set of determined capture thresholds for a plurality of occurrences of the electrode(s) sensing capture;
    memory for storing said determined capture thresholds; and wherein
    the microprocessor is further configured to determine a historical variability from the set of determined capture thresholds and set a safety margin based on the historical variability of the set of determined capture thresholds, and to determine a pacing pulse level based on the set safety margin for use in subsequently pacing the chamber of the patient's heart at the pulse level.

A thirty first embodiment relates to an implantable medical device of embodiment 30 wherein the memory is configured to store a first safety margin and a second safety margin, the first safety margin comprising adding a safety margin for a first time period and the second safety margin comprising adding the safety margin to a second time period.

A thirty second embodiment relates to an implantable medical device of embodiment 31 wherein the first time period is a 14 day maximum and the second time period is a current days measured threshold.

A thirty third embodiment relates to an implantable medical device of embodiments 30-32 wherein the processor is configured to automatically switch to the first safety margin in response to determining that historical indications is insufficient.

A thirty fourth embodiment that is directed to the implantable medical device of any of embodiments 30-33 wherein historical indications is a current threshold is higher than the current amplitude used for pacing.

A thirty fifth embodiment relates to the implantable medical device of any of embodiments 30-34 wherein the current threshold is one of a current amplitude threshold and a pulse width threshold.

A thirty sixth embodiment relates to the implantable medical device of 3 wherein the current amplitude threshold is at least one or more pacing capture threshold(s) measured over a third period of time.

A thirty seventh embodiment relates to the implantable medical device of embodiments 30-36 wherein the third period of time is at least one day.

A thirty eighth embodiment relates to the implantable medical device of embodiment 36 wherein the current amplitude threshold is used to determine a pacing amplitude.

It is recognized that those skilled in the art, having the benefit of the teachings provided herein, may conceive of numerous variations to the methods described herein for automatically adjusting a safety factor or a safety margin in response to various indicators of an increased pacing threshold. The embodiments described herein are intended to be exemplary, therefore, and not limiting with regard to the following claims.

The invention claimed is:

1. A method of providing capture management, the method comprising:
    (a) employing a cardiac pacemaker to determine capture thresholds of a chamber of a patient's heart;
    (b) storing into memory the determined capture thresholds;
    (c) determining a historical variability of the determined capture thresholds;
    (d) setting a safety margin using the historical variability of the determined capture thresholds; and
    (e) using the set safety margin to determine a pacing pulse level and subsequently employing the cardiac pacemaker to pace the chamber of the patient's heart at the pacing pulse level;
    wherein determining the historical variability of the determined capture thresholds comprises determining a rolling maximum and rolling minimum of the determined capture thresholds over a time period and determining a difference in amplitude between the rolling maximum and the rolling minimum; and
    wherein using the set safety margin to determine a pacing pulse level comprises selecting the safety margin in response to the difference in amplitude; and
    wherein the safety margin is set to a first value if the difference in amplitude between the rolling maximum and the rolling minimum is less than a second value.

2. A method according to claim 1 further comprising determining whether fewer than a pre-specified number of the determined capture thresholds are valid, and wherein if fewer than the pre-specified number of the determined capture thresholds are valid, the safety margin is set to a preset value.

3. A method according to claim 2 wherein the preset value is 1.5V.

4. A method according to claim 1 wherein the safety margin is set to a third value when the difference in amplitude between the rolling maximum and the rolling minimum is greater than the second value but less than a forth value.

5. A method according to claim 4 wherein the safety margin is set to a fifth value when the difference in amplitude between the rolling maximum and the rolling minimum is greater than the fourth value but less than a sixth value.

6. A method according to claim 1 wherein the time period is 14 or less consecutive days.

7. A method of providing capture management, the method comprising:
    (a) employing a cardiac pacemaker to determine capture thresholds of a chamber of a patient's heart;
    (b) storing into memory the determined capture thresholds;
    (c) determining a historical variability of the determined capture thresholds;
    (d) setting a safety margin using the historical variability of the determined capture thresholds; and
    (e) using the set safety margin to determine a pacing pulse level and subsequently employing the cardiac pacemaker to pace the chamber of the patient's heart at the pacing pulse level;
    wherein determining the historical variability of the determined capture thresholds comprises determining a rolling maximum and rolling minimum of the determined capture thresholds over a time period and determining a difference in amplitude between the rolling maximum and the rolling minimum; and
    wherein using the set safety margin to determine a pacing pulse level comprises selecting the safety margin in response to the difference in amplitude; and
    wherein the safety margin is set to 0.5V if the difference in amplitude between the rolling maximum and the rolling minimum is less than 0.5V.

8. A method of claim 7 wherein the time period is 14 or less consecutive days.

9. A method according to claim 7 wherein the safety margin is set to 1.0V when the difference in amplitude between the rolling maximum and the rolling minimum is ≥0.5V but less than 1.0V.

10. A method according to claim 7 wherein the safety margin is set to 1.5V when a difference in amplitude between the rolling maximum and the rolling minimum is ≥1.0V.

* * * * *